United States Patent [19]
Fujii et al.

[11] 4,308,201
[45] Dec. 29, 1981

[54] PHENYLALANYLVALYLARGININE DERIVATIVE, PROCESS FOR PRODUCING SAME AND METHOD FOR MEASURING ACTIVITY OF ENZYMES USING SAME

[75] Inventors: Setsuro Fujii, Toyonaka; Mamoru Sugimoto, Chiba; Takashi Yaegashi, Funabashi, all of Japan

[73] Assignee: Torii & Co., Ltd., Tokyo, Japan

[21] Appl. No.: 88,325

[22] Filed: Oct. 25, 1979

[30] Foreign Application Priority Data

Oct. 30, 1978 [JP] Japan ................................. 53-133395

[51] Int. Cl.³ ........................ C07C 103/52; C12Q 1/56
[52] U.S. Cl. ................................. 260/112.5 R; 435/13
[58] Field of Search ..................... 260/112.5 R; 435/13

[56] References Cited

U.S. PATENT DOCUMENTS 3,884,896  5/1975  Blomback et al. ............ 260/112.5 R
3,886,136  5/1975  Claeson et al. ............... 260/112.5 R

*Primary Examiner*—Delbert R. Phillips

*Attorney, Agent, or Firm*—Beveridge, DeGrandi, Kline & Lunsford

[57] ABSTRACT

A phenylalanylvalylarginine derivative represented by the formula,

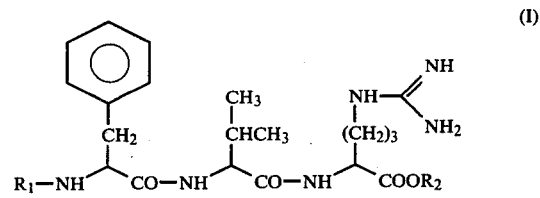

(I)

wherein $R_1$ represents hydrogen or benzoyl and $R_2$ represents naphthyl. The above compound is useful as an excellent substrate for various enzymes, such as trypsin, plasmin, kallikrein, urokinase, Cl-esterase and the like. Accordingly, the activity of enzymes can be measured by use of said compound as a substrate.

3 Claims, 3 Drawing Figures

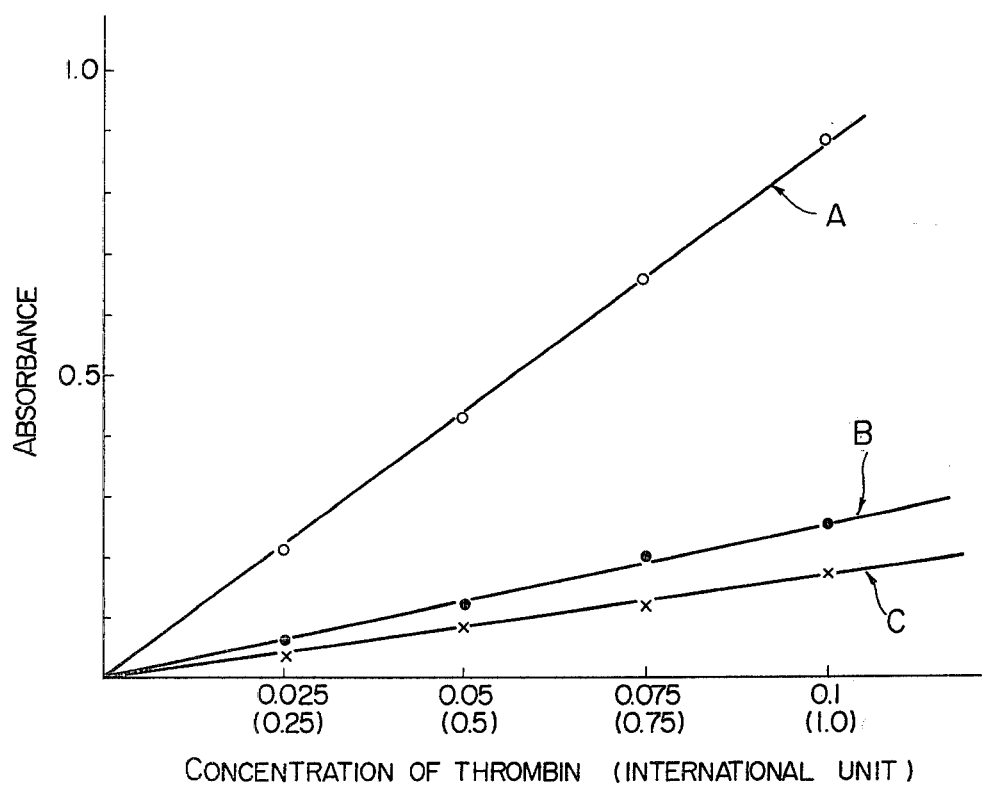

PHENYLALANYLVALYLARGININE DERIVATIVE, PROCESS FOR PRODUCING SAME AND METHOD FOR MEASURING ACTIVITY OF ENZYMES USING SAME

This invention relates to a novel phenylalanylvalylarginine derivative, a process for producing the same, and a method for measuring the activity of enzymes using the compound as a substrate.

Hitherto, many methods have been known for measuring the activity of enzymes. One of them is a method by which an alkyl ester of an amino acid is contacted as a substrate with an enzyme and the activity of the enzyme is determined from the degree of hydrolysis of the alkyl ester. For example, the well-known Hestrin method is one of the methods. This is a method which comprises contacting an enzyme with an alkyl ester of an amino acid, converting the remaining ester group after a given period of time with hydroxylamine into a hydroxamic acid, allowing it to react with ferric chloride to develop a color, and measuring the color as an absorbance, and determining the enzyme's ability to hydrolyze the ester, namely the activity of enzyme, from the absorbance.

In addition, there is a method in which paranitroanilaide of an amino acid is used as a substrate and the ability to hydrolyze the same is used as an index, or the like. In these methods, a considerable amount of an enzyme is required, and when the enzyme concentration is low or when the enzyme has a low activity, it has been difficult to measure the activity of enzyme.

The present inventors have conducted extensive research on compounds satisfying the following three conditions: They have an affinity to an enzyme, the determination of the amount of enzyme is easy, and the detection sensitivity of the compounds is good. Consequently, the inventors have found compounds useful as substrate which are very excellent as to the above conditions as compared with the conventional ones, and a simple method for measuring the activity of enzyme by use of the compounds.

An object of this invention is to provide a novel amino acid derivative which is useful as an excellent substrate for an enzyme.

Another object of this invention is to provide a process for producing the said novel amino acid derivative.

A further object of this invention is to provide a method for measuring the activity of an enzyme by use of said novel amino acid derivative as a substrate for the enzyme.

Other objects and advantages of this invention will become apparent from the following description.

According to this invention, there is provided a phenylalanylvalylarginine derivative represented by the formula,

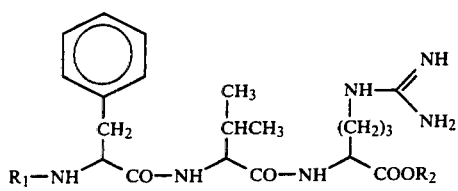

(I)

wherein $R_1$ represents hydrogen or benzoyl and $R_2$ represents naphthyl.

This invention further provides a process for producing a phenylalnaylvalylarginine derivative represented by the formula (I), which comprises subjecting to dehydration-condensation a compound (II) represented by the formula,

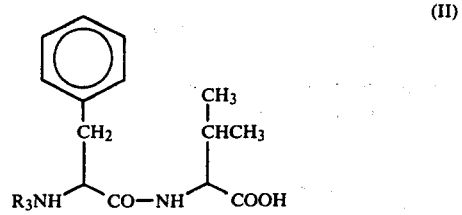

(II)

wherein $R_3$ represents benzoyl or an amino-protecting group, and an arginine derivative (III) represented by the formula,

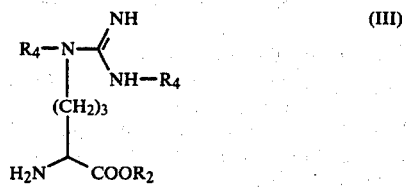

(III)

wherein $R_2$ has the same meaning as defined above and $R_4$ represents an amino-protecting group, in a conventional manner to obtain a compound (IV) represented by formula,

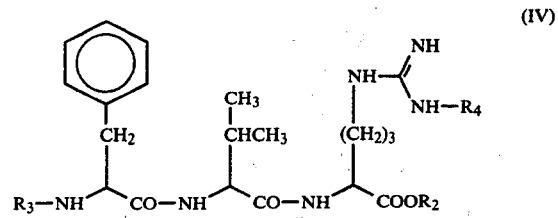

(IV)

wherein $R_2$, $R_3$ and $R_4$ have the same meanings as defined above, and then removing the amino-protecting group from the compound (IV) in a conventional manner.

According to this invention, there is also provided a method for measuring the activity of an enzyme, which comprises contacting the enzyme with a phenylalanylvalylarginine derivative represented by the formula (I) as a substrate.

The starting compound (II) used in the production of the compound (I) of this invention may be prepared by condensing a compound (V) represented by the formula,

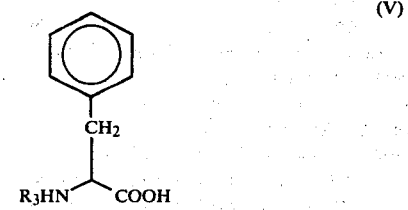

(V)

wherein $R_3$ has the same meaning as defined above, with a compound represented by the formula,

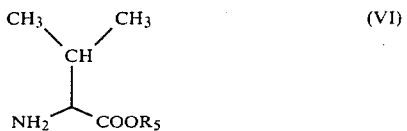

wherein $R_5$ represents alkyl, into an ester (VII) represented by the formula,

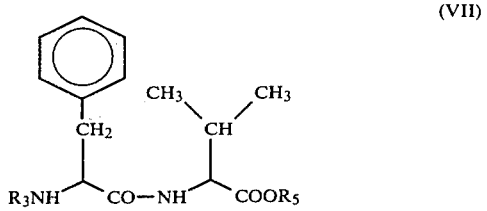

wherein $R_3$ and $R_5$ have the same meanings as defined above, and then hydrolyzing the ester (VII). Otherwise, the compounds disclosed in L. Lubiewska-Nakonieczna, B. Rzeszotarska and E. Taschner, Justus Liebigs Ann. Chem., 741, 157 (1970) may be used as the compound (II).

The starting arginine derivatives (III) includes $N^G,N^G$-dibenzyloxycarbonyl-L-arginine 1-naphthyl ester and the like, and may be prepared by naphthylating an arginine derivative (III') having a suitable protecting group represented by the formula,

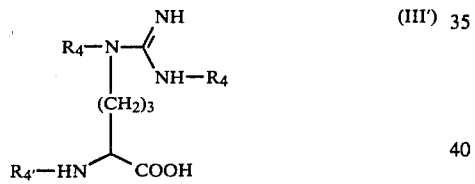

wherein $R_4$ has the same meaning as defined above, and $R_{4'}$ represents an amino-protecting group different from the $R_4$ group, to form a compound (III") represented by the formula,

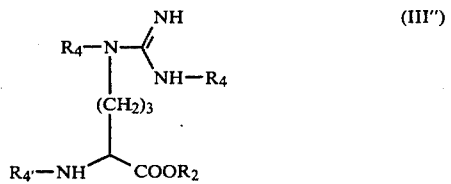

wherein $R_2$, $R_4$ and $R_{4'}$ have the same meanings as defined above, and then selectively removing only the amino-protecting group in the α-position from the compound (III").

In the production of the compound (IV), the compound (II) and the arginine derivative (III) are dissolved in a suitable solvent, and to the resulting solution is added an activating agent which is usually used, such as dicyclohexylcarbodiimide (DCC), diphenylphosphorylazide (DPPA), an alkyl chlorocarbonate or the like, after which, if necessary, a base such as triethylamine or the like is added thereto and the resulting mixture is stirred, thereby preparing the compound (IV). The solvent used includes conventional solvents, such as chloroforms, dichloromethane, dimethylformamide, tetrahydrofuran and the like as far as the starting materials can be dissolved therein. The reaction temperature may be within the range of 0° to 40° C.

After the completion of the reaction, the compound (IV) can be isolated from the reaction mixture by a conventional treatment. That is to say, when DCC is used as the activating agent, the dicyclohexylurea (DCU) precipitated is removed by filtration, and a suitable extracting solvent such as ethyl acetate is added to the filtrate, after which the extract is washed with an aqueous citric acid solution, saturated aqueous sodium bicarbonate solution or saturated aqueous sodium chloride solution, dried over anhydrous magnesium sulfate, and then evaporated under reduced pressure to remove the solvent to obtain the compound (IV).

The amino-protecting group of the compound (IV) is removed in a conventional manner. That is to say, when the amino-protecting group is benzyloxycarbonyl, the compound (IV) is dissolved in a suitable solvent and a catalyst such as palladium-carbon or the like is added to the resulting solution to remove the protecting group reductively, or the compound (IV) is added to a solution of hydrobromic acid in acetic acid and the hydrobromide of the objective compound precipitated is taken out by filtration, wereby the compound (I) is obtained.

The compound (I) of this invention is useful as an excellent substrate for various enzymes such as trypsin, plasmin, kallikrein, urokinase, Cl-esterase, thrombin and the like. That is to say, when the compound (I) of this invention is contacted with an enzyme, the compound serves as a substrate, and naphthol is liberated by hydrolysis with the enzyme after a given period of time, after which the amount of the naphthol is measured to determine the activity of the enzyme. The fact that the activity of an enzyme can be measured easily is very important for quantitative analysis of an enzyme preparation, diagonosis by measuring the enzyme pattern in blood, diagonosis by measuring the enzyme concentration in blood or urine, or the like.

When the activity of an enzyme is measured according to the process of this invention, the enzyme is contacted with a given amount of the compound (I) of this invention in a suitable buffer solution, and after a given period of time at a given temperature, the amount of naphthol liberated is measured, thereby determining the activity of the enzyme. The buffer solution may be a suitable one having the optimum pH for the enzyme. The reaction may be effected under suitable constant conditions as to temperature and time, though it is preferable to measure the amount of the naphthol liberated at a temperature of 25° to 37° C. after 30 min.

The measurement of the amount of naphthol may be conducted by any of the known methods, for example, a physicochemical method, such as, gas chromatography, thin layer chromatography, or the like; or a chemical method, such as, ferric chloride reaction, diazo-coupling reaction, Fast Violet B salt (FVB) method, or the like, though a method which comprises adding FVB to the reaction mixture to develop a color and measuring the absorbance by means of a photometer is more preferable in view of simplicity and detection sensitivity.

When the activity of thrombin is measured by use of N-bazoyl-L-phenylalanyl-L-valyl-L-arginine 1-naphthyl ester as a substrate according to the method of this invention, the sensitivity thereof is about 31 times that of Nα-tosyl-L-arginine methyl ester.

The amount of the naphthol measured by the method of this invention corresponds to the activity or amount of the enzyme.

According to the method of this invention, it is possible to detect a change in enzyme concentration in blood or urine due to various diseases with ease.

This invention is further illustrated below referring to Examples and the accompanying drawing, which shows standard curves of the concentration of thrombin.

EXAMPLE 1

Production of L-phenylalanyl-L-valyl-L-arginine 1-naphthyl ester dihydrochloride In 10 ml of N,N-dimethylformamide (DMF) were dissolved 796 mg of N-benzyloxycarbonyl-L-phenylalanyl-L-valine (refer to L. Lubiewska-Nakonieczna, B. Rzeszotarska and E. Taschner, Justus Liebigs Ann. Chem., 741, 157 (1970)) and 1.36 g of $N^G,N^G$-dibenzyloxycarbonyl-L-arginine 1-naphthyl ester trifluoroacetate, after which 533 mg of DCC, 351 mg of 1-hydroxybenzotriazole (HOBt) and 0.31 ml of triethylamine (TEA) were added to the solution with ice-cooling. The resulting mixture was stirred at the same temperature for 3 hrs and then stirred at room temperature for 24 hrs. After the reaction, the DCU thus precipitated was removed by filtration, and ethyl acetate was added to the filtrate. The resulting mixture was washed with 10% citric acid solution, saturated sodium bicarbonate solution and saturated sodium chloride solution in this order, dried over anhydrous magnesium sulfate, and then evaporated under reduced pressure to remove the solvent. The residue was recrystallized from ethyl acetate to obtain 810 mg (yield 43%) of white powder of N-benzyloxycarbonyl-L-phenylalanyl-L-valyl-$N^G,N^G$-dibenzyloxycarbonyl-L-arginine 1-naphthyl ester, m.p. 174°–176° C.

IR $\nu_{max}^{KBr}$ cm$^{-1}$: 3400, 3250, 1740, 1720, 1640.

NMR δppm (CDCl$_3$+DMSO-d$_6$): 0.9 (6H, d), 2.0 (4H, broad), 2.6 (1H, m), 3.1 (2H, m), 4.0–5.0 (1H×3, m), 5.0 (2H, s), 5.2 (2H, s), 5.3 (2H, s), 7.2–8.1 (aromatic protons).

In 5 ml of DMF was dissolved 720 mg of the above ester, and 300 mg of 10% palladium-carbon (Pd-C) and 0.80 g of hydrochloric acid-dioxane solution (98 mg HCl/g) were added to the solution. The resulting mixture was stirred for 3 hrs while passing hydrogen gas therethrough, after which the Pd-C was removed by filtration. To the filtrate was added 100 ml of anhydrous diethyl ether, and the white powder thus precipitated was collected to obtain 440 mg (yield 93%) of L-phenylalanyl-L-valyl-L-arginine 1-naphthyl ester dihydrochloride, m.p. 113°–118° C. (decomp.).

IR $\mu_{max}^{KBr}$ cm$^{-1}$: 3650, 1750, 1650.

The $N^G,N^G$-dibenzyloxycarbonyl-L-arginine 1-naphthyl ester trifluoroacetate used as the starting material was prepared as follows:

In 30 ml of anhydrous pyridine was dissolved 9.1 g of Nα-4-methoxybenzyloxycarbonyl-$N^G,N^G$-dibenzyloxycarbonyl-L-arginine (see Z. Naturf. 20b, 429 (1965) F. Weygand, E. Nintz.), and 7.9 g of 1,1'-dinaphthyl sulfite was added thereto. The resulting mixture was stirred at room temperature for 24 hrs. Ethyl acetate was added to the reaction mixture, and the mixture was washed with 10% citric acid solution, saturated sodium bicarbonate solution and saturated sodium chloride solution in this order, dried over anhydrous magnesium sulfate, and then evaporated under reduced pressure to dryness. The residue was washed with anhydrous diethyl ether to obtain 9.0 g (yield 82%) of pale yellow, vicous, oily substance of Nα-4-methoxybenzyloxycarbonyl-$N^G,N^G$-dibenzyloxycarbonyl-L-arginine 1-naphthyl ester.

IR $\nu_{max}^{KBr}$ cm$^{-1}$: 3400, 1760, 1720, 1690.

NMR δ ppm (CDCl$_3$): 1.9 (4H, m), 3.7 (3H, s), 4.1 (2H, m), 4.8 (1H, m), 5.1 (2H×2, s), 5.2 (2H, s), 6.7–8.0 (aromatic protons)

To 8.0 g of the above ester was added 15 ml of trifluoroacetic acid, and the resulting mixture was stirred for 30 min with ice-cooling. After the reaction, the reaction mixture was evaporated under reduced pressure to remove the trifluoroacetic acid, and anhydrous diethyl ether was added to the residue to dissolve the latter, after which the resulting solution was allowed to stand. The colorless needle crystals thus precipitated were collected to obtain 4.5 g (yield 61%) of $N^G,N^G$-dibenzyloxycarbonyl-L-arginine 1-naphthyl ester trifluoroacetate, m.p. 149°–151° C.

IR $\nu_{max}^{KBr}$ cm$^{-1}$: 3400, 1760, 1720, 1665.

NMR δ ppm (CDCl$_3$+DMSO-d$_6$): 2.1 (4H, m), 4.0 (2H, m), 4.5 (1H, m), 5.1 (2H, s), 5.2 (2H, s), 7.1–8.0 (aromatic protons).

EXAMPLE 2

Production of N-benzoyl-L-phenylalanyl-L-valyl-L-arginine 1-naphthyl ester hydrochloride In 15 ml of DMF were dissolved 368 mg of N-benzoyl-L-phenylalanyl-L-valine and 682 mg of $N^G,N^G$-dibenzyloxycarbonyl-L-arginine 1-naphthyl ester trifluoroacetate, after which 268 mg of DCC, 135 mg of HOBt and 0.14 ml of TEA were added to the resulting solution with ice-cooling. The resulting mixture was stirred at the same temperature for 3 hrs, and then stirred at room temperature for 24 hrs. The crystals thus precipitated were collected by filtration and then recrystallized from chloroform to obtain 600 mg (yield 63%) of N-benzoyl-L-phenylanayl-L-valyl-$N^G,N^G$-dibenzyloxycarbonyl-L-arginine 1-naphthyl ester, m.p. 163°–168° C.

IR $\nu_{max}^{KBr}$ cm$^{-1}$: 3300, 1745, 1720, 1630.

In 10 ml of DMF was suspended 0.5 g of the above ester, after which 200 mg of 10% Pd-C and 1.0 g of hydrochloric acid-dioxane solution (110 mg HCl/g) were added. The resulting mixture was stirred at room temperature for 2 hrs while passing hydrogen gas therethrough. The reaction mixture was filtered to remove the Pd-C, and 40 ml of anhydrous diethyl ether was added to the filtrate. The resulting mixture was allowed to stand for 24 hrs in iced water. The supernatant was removed by decantation, and 40 ml of anhydrous diethyl ether was added to the residue, and the resulting mixture was stirred to obtain 200 mg (yield 53%) of white powder of N-benzoyl-L-phenylalanyl-L-valyl-L-arginine 1-naphthyl ester hydrochloride, m.p. 75°–85° C. (decomp.).

IR $\nu_{max}^{KBr}$ cm$^{-1}$: 3200, 1750, 1640.

The N-benzoyl-L-phenylalanyl-L-valine used as the starting material was prepared as follows:

In 100 ml of tetrahydrofuran (THF) were dissolved 13.5 g of N-benzoyl-L-phenylalanine and 8.4 g of L-valine methyl ester hydrochloride, after which 13.8 g of DPPA and 14.0 ml of TEA were added to the solution with ice-cooling. The resulting mixture was stirred at room temperature for 24 hrs. The reaction mixture was evaporated under reduced pressure to dryness, and the residue was dissolved in ethyl acetate. The solution was washed with 10% citric acid solution, saturated sodium bicarbonate solution and saturated sodium chloride solution in this order, dried over anhydrous magnesium sulfate, and then evaporated under reduced pressure to dryness. The residue was recrystallized from ethyl acetate-n-hexane to obtain 7.3 g (yield 38%) of white powder of N-benzoyl-L-phenylalanyl-L-valine methyl ester, m.p. 160°–163° C.

IR $\nu_{max}^{KBr}$ cm$^{-1}$: 3300, 1730, 1630.

In 100 ml of methanol was dissolved 5.7 g of the above ester, and then 24 ml of 1 N NaOH solution was added to the solution. The resulting solution was stirred at room temperature for 2 hrs. The reaction mixture was concentrated under reduced pressure, and distilled water and ethyl acetate were added to the residue. The resulting mixture was shaken. The aqueous layer was separated, and made weakly acidic with 10% hydrochloric acid. The oily substrate thus precipitated was extracted with ethyl acetate and the extract was washed with water, dried over anhydrous magnesium sulfate, and then evaporated under reduced pressure to remove the solvent. The residue was recrystallized from ethyl acetate-n-hexane to obtain 3.0 g (yield 54%) of N-benzoyl-L-phenylalanyl-L-valine, m.p. 191° C.

IR $\nu_{max}^{KBr}$ cm$^{-1}$: 3350, 1710, 1630.

EXAMPLE 3

Measurement of the activity of thrombin by use of N-benzoyl-L-phenylalanyl-L-valyl-L-arginine 1-naphthyl ester hydrochloride as substrate To 1.7 ml of 50 mM phosphate buffer solution (pH 7.0) were added 0.1 ml of thrombin at various concentrations and 0.2 ml of N-benzoyl-L-phenylalanyl-L-valyl-L-arginine 1-naphthyl ester hydrochloride solution (1.5 mM), and the resulting mixture was subjected to incubation at 25° C. for 30 min. The mixture was cooled in iced water, and 0.1 ml of 1% FVB was added thereto. The resulting mixture was allowed to stand at 0° C. for 10 min, and 1 ml of glacial acetic acid was further added thereto. The color thus developed was measured as absorbance (505 nm) by means of a spectrophotometer, thereby determining the amount of the naphthol liberated by hydrolysis with the enzyme. As a control, the buffer solution same as above but free from thrombin was used. The amount of the naphthol liberated corresponded to the activity of the enzyme.

The results of measurement of absorbance at each thrombin concentration according to the above method are shown in the drawing.

COMPARATIVE EXAMPLE 1

Measurement of the activity of thrombin by use of Nα-tosyl-L-arginine ethyl ester hydrochloride as substrate To 0.1 ml of thrombin were added 0.3 ml of Nα-tosyl-L-arginine methyl ester hydrochloride solution (10 micromoles/0.4 ml of 5% DMSO) and 0.6 ml of phosphate buffer solution (pH 7.4), and the resulting mixture was subjected to incubation at 37° C. for 30 min, after which 1.5 ml of a hydroxylamine solution (a mixture of equal amounts of 2 M NH$_2$OH hydrochloride and 3.5 M NaOH) was added thereto. The resulting mixture was allowed to stand at room temperature for 15 min. Thereto were added 1 ml of 18% trichloroacetic acid solution, 1 ml of 4 N hydrochloric acid, and 1 ml of 10% ferric chloride solution. The resulting mixture was thoroughly stirred and then centrifuged at 3,000 r.p.m. for 10 min. The color thus developed of the supernatant was measured as absorbance (530 nm) by means of a spectrophotometer. The value obtained corresponds to the amount of the substrate remaining unhydrolyzed with thrombin, and therefore, and activity of the enzyme corresponds to the difference between the value obtained when no enzyme was used (control) and the value obtained after the enzyme reaction.

COMPARATIVE EXAMPLE 2

Measurement of the activity of thrombin by use of N-benzoyl-L-phenylalanyl-L-valyl-L-arginine p-nitroanilide hydrochloride To 2.15 ml of 0.1 μM tris HCl buffer solution (pH 8.0) were added 0.1 ml of thrombin at various concentrations and 0.25 ml of an N-benzoyl-L-phenylalanyl-L-valyl-L-arginine p-nitroanilide hydrochloride solution (1mM/H$_2$O), and the resulting mixture was subjected to incubation at 37° C. for 30 min. To the mixture was added 0.3 ml of glacial acetic acid, and the color developed was measured as absorbance (405 nm) by means of a spectrophotometer.

The results of measurement in Example 3, Comparative Example 1 and Comparative Example 2 are shown in the drawing, from which it can be seen that the method of Example 3 has a detection sensitivity about 30 times that in Comparative Example 1 and about 5 times that in Comparative Example 2.

In the drawing, curve A refers to a standard curve obtained in Example 3, curve B to a standard curve obtained in Comparative Example 1, and curve C to a standard curve obtained in Comparative Example 2. The numbers in the paretheses on the abscissa indicate the enzyme concentrations for curve B.

The following Table shows the relative sensitivity when the activity of other enzymes was measured according to the methods of Example 3 and Comparative Example 2.

TABLE

| | Enzyme | | | | |
| | Thrombin | Kallikrein | | Factor | |
| Substrate | | Plasma | Tissue | Xa | Urokinase |
| --- | --- | --- | --- | --- | --- |
| N-benzoyl-L-phenylalanyl-L-valyl-L-arginine 1-naphthyl ester | 5.0 | 12.5 | 30 | 15 | 40 |
| N-benzoyl-L-phenylalanyl-L-valyl-L-arginine p-nitroanilide | 1.0 | 1.0 | 1.0 | 1.0 | 1.0 |

What is claimed is:

1. A phenylalanylvalylarginine derivative represented by the formula,

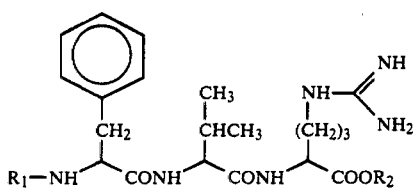 (I)
wherein $R_1$ represents hydrogen or benozyl and $R_2$ represents naphthyl.
2. L-phenylalanyl-L-valyl-L-arginine 1-naphthyl ester.
3. N-benzoyl-L-phenylalanyl-L-valyl-L-arginine 1-naphthyl ester.
* * * * *